United States Patent [19]

Wong et al.

[11] Patent Number: 5,329,025
[45] Date of Patent: Jul. 12, 1994

[54] 3-AZIDO COMPOUND

[75] Inventors: Chi-Huey Wong; Richard L. Pederson; Yi-Fong Wang, all of College Station, Tex.

[73] Assignee: G. D. Searle & Co., Chicago, Ill.

[21] Appl. No.: 862,157

[22] Filed: Apr. 2, 1992

Related U.S. Application Data

[62] Division of Ser. No. 247,276, Sep. 21, 1988, abandoned.

[51] Int. Cl.$^5$ .................. C07C 247/02; C07C 247/00; C07C 205/05; C07C 207/00
[52] U.S. Cl. ......................... 552/10; 552/1; 568/423
[58] Field of Search ...................... 435/122; 548/960; 534/550; 552/1, 10; 568/423

[56] References Cited

U.S. PATENT DOCUMENTS

| | | | |
|---|---|---|---|
| 4,266,025 | 5/1981 | Kinast et al. | 435/122 |
| 4,405,714 | 9/1983 | Kinast et al. | 435/84 |
| 4,806,650 | 2/1989 | Schroder et al. | 546/242 |

OTHER PUBLICATIONS

S. Inouye et al. Structure and Synthesis of Nojirimycin Tetrahedron Letters vol. 23 2125–2144 Jan. 1968.
G. Kinast et al. A Four-Step Synthesis of 1-Deoxynojirimycin etc. Angew. Chem. Int. Ed. Engl. vol. 20 No. 9 805–806 Jan. 1981.
Durrwachter et al. Enzymatic Aldol Condensation/Isomerization as etc. J. Am. Chem. Soc. 108 7812–7818 Jan. 1986.
Effenberger et al. A Novel Convenient Preparation of etc. Tetrahedron Letters vol. 28 No. 15 1641–1644 Jan. 1987.
Pederson et al. A Combined Chemical & Enzymatic Procedure for etc. Tetrahedron Letters vol. 29 No. 37 4645–4648 Jan. 1988.
Thomas Ziegler et al Enzyme-Catalyzed Synthesis of etc. Angew, Chem. Int. Ed. Engl. vol. 27 No. 5 716–717 Jan. 1988.
E. Truscheit et al. Chemistry and Biochemistry of Microbial etc. Angew, Chem. Int. Ed. Engl. vol. 20 744–761 Jan. 1981.
Fleet et al. Synthesis of 1,5-Dideoxy-1,-5-Imino-D-Mannitol etc. Tetrahedron Letters vol. 25 No. 36 4029–4032 Jan. 1984.
Fleet et al. Enantiospecific Syntheses of etc. Tetrahedron Letters vol. 26 No. 11 1469–1472 Jan. 1985.
Wong et al. Synthesis of Sugars by Aldolase-Catalyzed etc. J. Org. Chem. 48 3199–3205 Mar. 1983.
Wong et al. Chemical and Enzymatic Syntheses of etc. J. Org. Chem. 48 3493–3497 Jan. 1983.
Bednarski et al. Aldolase-Catalyzed Synthesis of Complex C8 and etc. Tetrahedron Letters vol. 27 No. 48 5807–5810 Jan. 1986.
Durrwachter et al. Fructose 1,6-Diphosphate Aldolase Catalyzed etc. J. Org. Chem. 53 4175–4181 Mar. 1988.

*Primary Examiner*—Douglas W. Robinson
*Assistant Examiner*—L. Blaine Lankford
*Attorney, Agent, or Firm*—Cynthia S. Kovacevic; Roger A. Williams

[57] ABSTRACT

A new and practical method for synthesizing heterocyclic polyhydroxylated alkaloids using enzymatic aldol condensation and catalytic intramolecular reductive amination is disclosed.

2 Claims, No Drawings

3-AZIDO COMPOUND

This is a division of application Ser. No. 07/247,276, filed Sep. 21, 1988, now abandoned.

BACKGROUND OF THE INVENTION

Polyhydroxylated alkaloids, such as 1-deoxynojirimycin, 1-deoxymannojirimycin, and 1,4-dideoxy-1,4-imino-D-arabinitol, are useful for treatment of carbohydrate-dependent metabolic disorders because of their selective inhibition of glycosidases. Truscheit, E., Frommet, W., Junge, B., Muller, L., Schmidt, D. D., Wingender, W. *Angew. Chem.* 93 (1981) 738; *Angew. Chem., Int. Ed. Engl.* 20 (1981) 744. Many polyhydroxylated alkaloids are natural products. For example, 1-deoxynojirimycin has been isolated from plants of genus Morus, Yagi, M., Kouno, T., Aoyagi, Y., Murai, H. *Nippon Nogei Kagaku Kaishi* 50 (1976) 571; Vasella, A., Voeffray, R. *Helv. Chim. Acta.* 65 (1982) 1134; 1-deoxynojirimycin also has been isolated from strains of Bacillus, Daigo, K., Inamori, Y., Takemoto, T. *Chem. Pharm Bull.* 34 (1986) 2243; and, 1-deoxymannojirimycin has been isolated from the legume of Lonchocarpus. Fellow, L. E., Bell, E. A. *JCS Chem. Comm.* (1979) 977.

Because isolation of these compounds from nature very often is time consuming and relatively expensive, several methods have been developed for preparing these valuable compounds. For example, the synthesis of 1-deoxynojirimycin most often starts with natural sugars. Inouye, S., Tsunuoka, T., Ito, T., Niida, T. *Tetrahedron* 24 (1968) 2125; Paulsen, H., Sangster, I., Heyns, K. *Chem,. Ber.* 100 (1967) 802; Saeki, H., Ohki, E. *Chem. Pharm. Bull.* 16 (1968) 2477; Paulsen, H., Tadt, K. *Adv. Carbohydr. Chem.* 23 (1968) 115; Kinast, G., Schedel, M. *Angew Chem. Int. Ed. Engl.* 20 (1981) 805; Bernotas, R. C., Ganem, B. *Tetrahedron Lett.* 25 (1984) 165; Bernotas, R. C., Ganem, B. Ibid, 26 (1985) 1123; Setoi, H., Takeno, H., Hashimoto, M. *Chem, Pharm. Bull.* 34 (1986) 2642; Iida, H., Yamazaki, N., Kibayshi, C. *J. Org. Chem.* 52 (1987) 3337. Usually, 1-deoxymannojirimycin is synthesized using D-glucose or L-tartrate. Seebach, D., Hungerbuhler "Modern Synthetic Methods" (1980), Scheffold, R., Ed., Salle and Sauerlander-Verlag: Frankfurt and Aarau 2 (1980) 91–171. Synthesis of 1-deoxymannojirimycin starts with D-mannose. Fleet, G. W. J., Smith, P. *Tetrahedron Lett.* 26 (1985) 1469; Fleet, G. W. J., Gough, M. J., Shing, T. K. M. Ibid. 25 (1984) 4029. Of the processes used up to this time, the most efficient are considered to be the combined microbial oxidation/intramolecular reductive amination for 1-deoxynojirimycin, Kinast, G., Schedel, M. *Angew Chem. Int. Ed. Engl.* 20 (1981) 805, and intramolecular aminomercuration for both 1-deoxynojirimycin and 1-deoxymannojirimycin.

Studies have shown that enzymes such as fructose-1,6-diphosphate (FDP) aldolase can be useful in the synthesis of unusual sugars. Studies on FDP aldolase as a catalyst in enzymatic aldol condensation indicate that the enzyme is very specific for dihydroxyacetone phosphate (DHAP) (or dihydroxyacetone in the presence of arsenate) as the aldol donor, but accepts a variety of aldehydes as acceptors. Wong, C-H, Whitesides, G. M. *J. Org. Chem.* 48 (1983) 3199; Wong, C-H., Mazenod, F. P., Whitesides, G. M. Ibid. 48 (1983) 3493; Durrwachter, J. R., Drueckhammer, D. G., Nozaki, K., Sweers, H. M., Wong, C-H. *J. Am. Chem. Soc.* 108 (1986) 7812; Bednarski, M. D., Waldmann, H. J., Whitesides, G. M. *Tetrahedron Lett.* 27 (1986) 5807. The stereochemistry of the newly formed C—C bond is completely controlled by the FDP aldolase and is the same in all cases.

SUMMARY OF THE INVENTION

The present invention generally comprises a method for synthesizing heterocyclic polyhydroxylated alkaloids using enzymatic aldol condensation and catalytic intramolecular reductive amination. In the present method, dihydroxyacetone phosphate, or dihydroxyacetone (in the presence of arsenate), is enzymatically condensed with an N-containing aldehyde acceptor to form an N-containing polyhydroxylated ketose phosphate, or an N-containing polyhydroxylated ketose, respectively. In the case of the N-containing polyhydroxylated ketose phosphate, the phosphate group is removed enzymatically before the next step, hydrogenation. Hydrogenation then is performed to result in a heterocyclic polyhydroxylated alkaloid. It will be apparent that the selection of the N-containing aldehyde acceptor will depend upon the ring structure of the desired product.

Several specific examples of the invention are described. In some of the examples, a racemic mixture of a chiral N-containing aldehyde acceptor is used as a starting product. In these examples, the reaction can be thermodynamically or kinetically controlled to select a desired diastereomeric product, thereby avoiding the need to separate the diastereomers. In other examples, a chiral, optically active N-containing aldehyde acceptor is used, resulting in only one diasteromer. A non-chiral N-containing aldehyde acceptor also can be used to result in a single product.

DETAILED DESCRIPTION OF THE INVENTION

In the following experiments, FDP aldolase, an enzyme with wide substrate specificity, was used. The FDP aldolase and other enzymes and biochemicals were purchased from Sigma, and can be purchased from a number of known sources. FDP aldolase alternatively can be isolated from other sources, such as bacteria or yeast. (E.g., *E. coli*-Baldwin, S. A., Perham, R. N., Stribling, O. *Biochem. J.* 169 (1978) 633, incorporated herein by reference; yeast-Richards, O. C., Rutter, W. J. *J. Biol. Chem.* 236 (1961) 3177, incorporated herein by reference.) The solvents and chemicals used were of reagent grade. Optical rotations were measured on a Perkin-Elmer 240 polarimeter. Proton, $^{13}C$, fluorine NMR spectra were obtained on Varian XL-200 or XL-400 spectrometers operating at 200, 400, 50 and 376 MHz, respectively. All chemical shifts are reported in ppm with tetramethylsilane as an internal standard unless otherwise indicated. UV spectra were taken with a Beckman DU-70 instrument. HPLC analyses were done on a Gilson chromatography system including a model 302 pump, model 101 refractive index detector, and a Rheodyne injector. Gas chromatography (GC) analyses were performed on a Hewlett-Packard 5890 instrument.

One of the required starting materials in the following reactions is an N-containing aldehyde acceptor having a predetermined structure. Novel N-containing aldehyde acceptors have been prepared in optically pure form by enzymatic resolution using the inexpensive enzyme lipase, as described in Example 4. Lipase accepts a wide range of substrates. The small amounts of undesired isomer resulting from the resolution can be recycled by conversion to the racemic starting material using known chemical procedures, for example, oxidation, reduction and acylation.

In the following examples, a protected form of a desired N-containing aldehyde acceptor, preferably a dialkylacetal derivative, is deprotected, for example, by hydrolysis. Dihydroxyacetone phosphate, or dihydroxyacetone and at least a catalytic amount of arsenate, is added in solution. Dihydroxyacetone phosphate can be purchased from chemical companies, such as Sigma, at a relatively high price. Dihydroxyacetone phosphate also can be prepared in situ from FDP-Na$_3$ in the presence of FDP aldolase and triosephosphate isomerase (TPI) according to the procedure described in Durrwachter, J. R., Drueckhammer, D. G., Nozaki, K., Sweers, H. M., Wong, C-H. *J. Am. Chem. Soc*, 108 (1986) 7812, incorporated herein by reference. Alternately, less expensive dihydroxyacetone (DHA) can be used along with at least a catalytic amount of arsenate. The rate of the reaction will increase with the amount of arsenate that is present in the solution up to a stoichiometric amount. FDP aldolase also is added in solution, or can be immobilized on a resin and exposed to the solution. The pH of the solution is adjusted to between 6–8, preferably 7.

The resulting N-containing polyhydroxylated ketose, or N-containing polyhydroxylated ketose phosphate, relatively unstable intermediates (or "aldol products") that can be protected by a reduceable or hydrolyzable function, is collected. Where the intermediate is a phosphate derivative, the product is collected by precipitation, and where the intermediate is unphosphorylated, the product is collected using centrifugation, collection, and evaporation of supernatant fractions. When present, the phosphate moiety is removed using acid phosphatase as described in Durrwachter, J. R., Drueckhammer, D. G., Nozaki, K., Sweets, H. M., Wong, C-H. *J. Am. Chem. Soc.* 108 (1986) 7218, incorporated herein by reference. The resulting N-containing polyhydroxylated ketose is collected, isolated, for example, using lyophilization, dissolved in an organic solvent such as methanol, evaporated, loaded to a Dowex 50 (Ba$^{+2}$) column, and eluted with an appropriate solvent, such as a mixture of ethanol and water.

The fractions containing N-containing polyhydroxylated ketose are evaporated, redissolved in approximately ½ of the product volume of a volatile organic solvent such as methanol, and hydrogenated. Hydrogenation is accomplished using Pd/C, preferably 10%, The rate of the reaction is dependent upon the amount of Pd/C that is used and the pressure at which the hydrogenation takes place, preferably 40–50 psi. The catalyst is removed by filtration, methanol is removed under reduced pressure, and the remaining solution is further concentrated and chromatographed. The fractions with product are collected and lyophilized to yield the desired heterocyclic polyhydroxylated alkaloid.

Where a chiral, optically pure N-containing aldehyde acceptor is used, the corresponding optically pure heterocyclic polyhydroxylated alkaloid is the sole product. Where the product includes multiple diastereomers such as 1-deoxynojirimycin and 1-deoxymannojirimycin, separation of the diasteromers can be accomplished using chromatography. In the case of 1-deoxynojirimycin and 1-deoxymannojirimycin, it has been found that separation can be achieved using chromatography on a Dowex 50 (Ba$^{+2}$) column with water as the mobile phase. It also has been found that the formation of heterocyclic polyhydroxylated alkaloids by the present method can be thermodynamically and kinetically controlled to select the desired diastereomeric product.

EXAMPLE 1

Preparation of 1-Deoxynojirimycin and 1-Deoxymannojirimycin

The general scheme of the following reactions is:

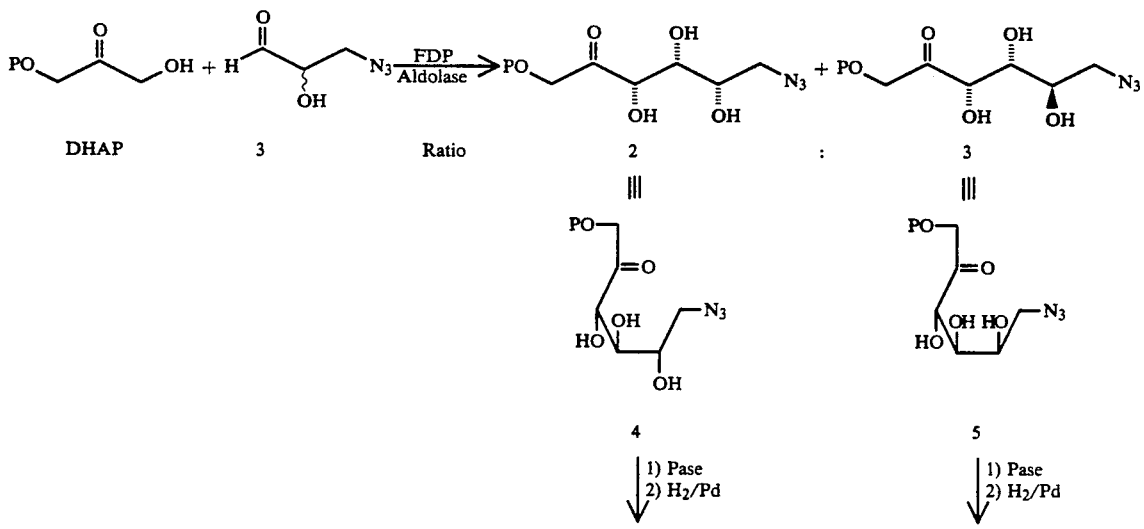

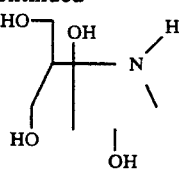
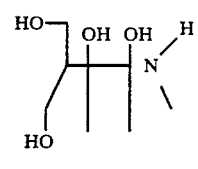

(a) (D,L)-3-azido-2-hydroxypropanal-diethyl acetyl

Into a 3-neck flask fitted with a stirring bar and pH probe was placed glycidaldehyde diethyl acetal (17.59 g, 102 mmol, 85% pure), 50% ethanol in water (250 ml), and $NaN_3$ (13.35 g, 205 mmol). The pH was adjusted to and maintained at 7.5 with aqueous $H_2SO_4$. The higher the pH, the faster the reaction, and the pH should be no lower than approximately 5.0 and no higher than approximately 10.0. The solution was warmed to 50° C. for twelve hours. GC analysis (40° C., 5 min to 250° C. at 15° C./minute, DB-5, $t^R$ of epoxide 5.65 min, product 10.0 min) indicated complete reaction. The ethanol was removed under reduced pressure, and the aqueous solution was saturated with $Na_2SO_4$. Removal of solvent by evaporation followed by distillation of residue yielded (D,L)-3-azido-2-hydroxypropanal-diethyl acetal, an aldehyde precursor having the following structure:

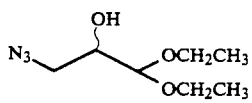

(D,L) -3-azido-2-hydroxypropanal

To a solution of 3-azido-2-hydroxypropanal-diethyl acetal (5.4 g, 28.6 mmol) in 50 mL of water was added conc. HCl (0.7 mL) to hydrolyze, or deprotect, the acetal. The solution was stirred at 45° C. for 36 h. The temperature can vary up to around 60°–70° C., the time needed to complete the reaction being shorter at higher temperatures. GC analysis (J&W Scientific DB-5 column (15 m×0.5 mm), 40° C. for 1 min to 250° C. at 20° C./min) showed complete hydrolysis of acetal ($R_t$ of starting material 6.33 min, that of product 2.65 min).

1-Deoxynojirimycin and 1-Deoxymannojirimycin

To obtain FDP-$Na_3$, FDP-Ca (Sigma) was dissolved in 20 mL of water, and the pH was adjusted to 1.5 with Dowex 50(H+). The pH can vary between approximately 1–3, but, preferably should be around 1.5. The solution was filtered and the pH was readjusted back to 7.0 with 2N NaOH. The pH can vary between approximately 6–8, but preferably should be adjusted to 7.0. The cloudy solution was filtered through a glass fritted funnel containing Celite 545 and lyophilized. The white powder was assayed enzymatically for FDP according to the processes described in Bergmeyer, H. U. "Methods of Enzymatic Analysis," Academic Press: New York (1974), and was shown to be 86% pure. FDP-$Na_3$ (4.4 mmol, 86% purity) then was added to the hydrolyzed acetal solution and the pH of the solution was adjusted from pH 2.5 to pH 6.5 with 2N NaOH. The pH can vary between approximately 6–8, but preferably should be 6.5.

Rabbit muscle FDP aldolase (400 U) and triosephosphate isomerase (500 U) were added (the two enzymes were used to generate 2 equivalents of DHAP in situ from FDP) and the solution was stirred slowly for 12 h. The amount of FDP aldolase and triosephosphate isomerase used at least must be a catalytic amount, and the rate of reaction increases as the amount of enzyme is increased. To the solution was added $BaCl_2 \cdot 2H_2O$ (5.3 g, 21 mmol) and 2 equivalent volumes of acetone (approximately 100 mL) to precipitate the phosphate. The amount of $BaCl_2 \cdot 2H_2O$ that is used at least must be equivalent to the amount of organic phosphate. The mixture was placed in a freezer at −20° C. overnight. The storage temperature is not critical and can vary between approximately −20° C.−4° C. The precipitated product was recovered and treated with Dowex 50 (H+) in 100 mL water to remove $Ba^{+2}$. The solution then was adjusted to pH 4.8 and acid phosphatase (300 U) was added and incubated at 38° C. overnight. The storage temperature can vary between approximately 25°–40° C., and the rate of reaction, again, increases with the amount of enzyme used. Ames test was performed according to the methods of *Methods Enzymol.* Vol. VIII (1966) 115–18. The Ames test for phosphate indicated 100% hydrolysis of the phosphate ester. The solution was readjusted back to pH 7.0 (which can be varied between approximately 6–8) and lyophilized to give a yellowish product, which was treated with methanol (2×50 mL) and filtered to remove insoluble material.

Evaporation of the methanol gave a product, which showed a single spot on TLC ($R_f$=0.71, EtOAc:-MeOH:$H_2O$=12:6:2). The precursor product was passed through a Dowex 50 ($Ba^{+2}$) 100–200 mesh column, using a mixture of ethanol and water (1:1) as the mobile phase. The fractions with precursor product were combined and the ethanol was removed under reduced pressure. To the remaining solution was added ¼ of its volume of methanol and the solution was hydrogenated with 300 mg 10% Pd/C under 40 psi of hydrogen for 10 h. Once again, the amount of Pd/C used affects the rate of the reaction, as does the pressure, which preferably should be between 40–50 psi. The catalyst was removed by filtration and the methanol was removed under reduced pressure. The remaining solution was concentrated to 5 mL and chromatographed on a Dowex 1 ($OH^-$) column. The fractions with product were collected and lyophilized to yield 0.851 g, 59% yield (based on FDP) of a white compound. $^{13}$C-NMR indicated a 1:4 ratio of 1-deoxynojirimycin to 1-deoxymannojirimycin. $^1$H-NMR and $^{13}$C-NMR were consistent with reported values. Fellows, L. E., Bell, E. A. *JCS Chem. Comm.* (1979) 977. Optical rotations also were consistent with reported values. Inouye, S., Tsunuoka, T., Ito, T., Niida, T. *Tetrahedron*, 24 (1968) 2125.

Separation of 1-deoxynojirimycin and 1-deoxymannojirimycin can be done with chromatography on a Dowex 50 (Ba$^{+2}$) column (3.0×97 cm) using water as a mobile phase.

(b) A solution (50 mL) containing 3-azido-2-hydroxypropanal (12 mmol, prepared as described in Example 1(a)), FDP-Na$_3$ (3 mmol, prepared as described in Reimer, L. M., Conley, D. L., Pompliano, D. L., Frost, J. W. *J. Am. Chem. Soc.* 108 (1986) 8010, incorporated herein by reference), FDP aldolase from *E. coli* (16 U), triosephosphate isomerase (500 U from Sigma), and ZnCl$_2$ (0.3 mM) at pH 6.5 was stirred slowly for 48 h. The products were recovered as their barium salt, and the phosphate moiety was removed by treatment with phosphatase as described in Durrwachter, J. R., Drueckhammer, D. G., Nozaki, K., Sweets, H. M., Wong, C-H. *J. Am. Chem. Soc.* 108 (1986) 7812, incorporated herein by reference. The sugars obtained then were hydrogenated in 28% MeOH with 300 mg 10% Pd/C under 40 psi of hydrogen for 10 h. The solution was filtered, concentrated to 4 mL and chromatographed on a Dowex 50 (Ba$^{+2}$) column (3.0×97 cm) with water as the mobile phase. 1-deoxynojirimycin was eluted first (284–310 mL) followed by 1-deoxymannojirimycin (356–430 mL). Lyophilization of the corresponding fractions yielded 1-deoxynojirimycin (0.24 g, 25% yield, [α]D$^{25}$=+47.5 (c 0.2 H$_2$O)) and 1-deoxymannojirimycin (0.4 g, 47% yield; [α]D$^{25}$=−29 (c 0.2, MeOH)). The $^1$H-NMR spectra, optical rotation and microanalyses are in agreement with the reported values. See, e.g., Morrison, J. F., Walsh, C. T. *Adv. Enzymology* (1988) 201 (slow-binding enzyme inhibitors); Truscheit, W., Frommet, B., Jung, L., Muller, L., Schmidt, D. D., Windgender, W. *Angew. Chem. Int. Ed. Engl.* 20 (1981) 755; Inouye, S., Tsunuoka, T., Ito, T., Niida, T. *Tetrahedron* 24 (1968) 2125 (example of another synthesis of deoxynojirimycin); Fleet, G. W. J., Smith, P. *Tetrahedron Lett.* 26 (1985) 1469 (example of another synthesis of 1-deoxymannojirimycin).

The ratio of 1-deoxynojirimycin to 1-deoxymannojirimycin increased when the aldol reaction proceeded, indicating a kinetic preference of (R)-3-azido-2-hydroxypropanal over (S)-3-azido-2-hydroxypropanal. When dihydroxyacetone phosphate was replaced with a mixture of dihydroxyactone and 0.5M sodium arsenate, the aldol condensation slowed by a factor of 5 and the kinetic product (1-deoxymannojirimycin) was obtained predominately in a ratio of 7:3 at different periods of time. This result was expected, as the reverse reaction (i.e., aldol cleavage) in this case should be much slower than the forward reaction.

EXAMPLE 2

Preparation of 1,4-dideoxy-1,4-amino-D-arabinitol

The general scheme of the following reaction is:

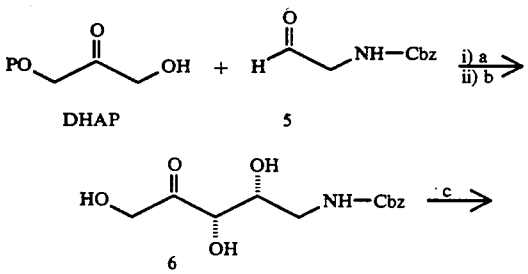

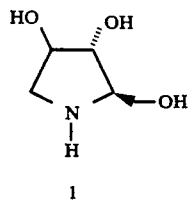

a = FDP aldolase
b = acid phosphatase
c = H$_2$/Pd

N-Benzyloxycarbonyl Aminoacetaldehyde Dimethyl Acetal

To a 50 ml solution of acetone and water (7:3) was added 1.60 g (15.2 mmol) aminoacetaldehyde dimethyl acetal and 3.83 g (45.6 mmol) sodium bicarbonate, and the solution was cooled to 4° C. Added dropwise was 2.28 ml (15.2 mmol) N-benzyloxycarbonyl chloride. After addition was complete, the solution was stirred for 4 hrs. The acetone was removed under reduced pressure and the remaining solution was extracted with ether (3×50 ml). The ether was removed under reduced pressure and the remaining solution was purified by flash chromatography (using hexane and ether 8:2 then 2:1) to yield 3.26 g of the titled compound 92% yield.

N-Benzyloxycarbonyl Aminoacetaldehyde

To a solution of 80 ml THF, 40 ml water, and 800 mg oxalic acid was added 9.6 g (40 mmol) of N-benzyloxycarbonyl aminoacetaldehyde dimethyl acetal, and refluxed for 4 days. The THF was removed under reduced pressure and the remaining solution was extracted with ether (3×100 ml), the ether fractions were combined and dried over anhydrous sodium sulfate. The ether was removed under reduced pressure and the remaining solution was purified by flash chromatography (hexane and ethyl acetate 3:1 then 1:1) to yield 3.88 g, 50% yield.

1,4-Dideoxy-1,4-Imino-D-Arabinitol

To a 100 ml round-bottomed flask containing a magnetic stirbar and 56 ml of a 86 mM solution of DHAP (4.8 mmol) at pH 7.0, was added 2.04 g (10.5 mmol) of N-benzyloxycarbonyl aminoacetaldehyde in 11.5 ml of DMSO. Upon addition of N-benzyloxycarbonyl aminoacetaldehyde in DMSO, the solution turned milky white and remained white during the entire reaction. FDP aldolase (200 U) was added and the solution was stirred for 18 hrs. Barium chloride 4.40 g (18.0 mmol) was added and the pH adjusted to 8.0 with 2N NaOH. Two equivalent volumes of acetone (200 ml) were added and the solution was stored at 0° C. for 6 hours. The precipitate was isolated and washed twice with cold acetone by centrifuging (15 min. at 3000 RPM). The precipitate was suspended in 200 ml of water and treated with Dowex 50 (H+) until the pH remained at 1.5. The solution was filtered, the pH adjusted to 4.8 with 2N NaOH, acid phosphatase (200 U) was added and the mixture was incubated at 37° C., with stirring, for 18 hrs. Ames test for phosphates (Ames, B. N. *Methods Enzymol.* Vol. VIII (1968) pp. 115–18) indicated 100% hydrolysis of the phosphate ester. The pH was readjusted to 7.0 and lyophilized.

The semi-solid residue was treated with methanol (3×50 ml) and filtered to remove insoluble material. The methanol was removed under reduced pressure until ≃10 ml remained. 20 ml of water and 1.0 g of 10% Pd/C was added. The solution was hydrogenated over 50 psi H₂ for 24 hrs. The Pd/C was removed by filtering and the solvent removed under reduced pressure. 1,4-dideoxy-1,4-imino-D-arabinitol was purified by recrystallizing the hydrochloride salt from methanol:ether (11:1) to obtain 241 mg, 28% yield (based on DHAP). $^1$H and $^{13}$C-NMR, optical rotation and melting point are consistent with reported values. Fleet, G. W. J., Nicholas, S. J., Smith, P. W., Evans, S. V., Fellows, L. E., Nash, R. J. *Tetrahedron Lett.* 26 (1985) 3127;Nash, R. J., Bell, E. A. *Phytochemistry* 24 (1985) 1620. The low yield is attributed to the poor water solubility of N-benzyloxycarbonyl aminoacetaldehyde. It is worth noting that the free base is a hygroscopic oil, the corresponding hydrochloride is crystalline and relatively easy to handle.

EXAMPLE 3

Preparation of Fagomine

Fagomine was prepared by the same procedure described in Example 2, as diagrammed below:

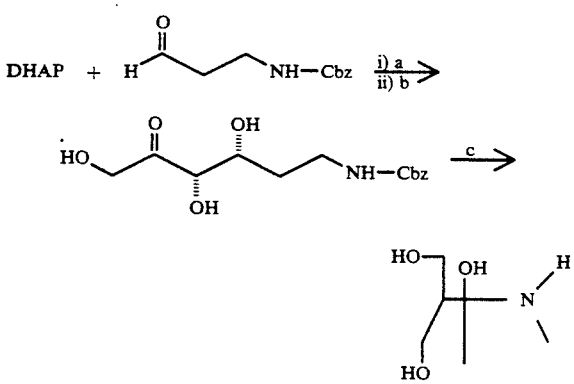

a = FDP aldolase
b = acid phosphatase
c = H₂/Pd

The product was purified by silica gel column chromatography to yield 350 mg of fagomine, 34% yield (based on DHAP). $^1$H-NMR, optical rotation and melting point are consistent with reported values. Kayama, M., Sakamura, S. *Agr. Biol. Chem.* 38 (1974) 1111. The $^{13}$C-NMR shifts of fagomine are the following: 50 MHz, D₂O δ 71.6, 71.2 (C3, C4), 60.4, 59.4 (C5, C6), 42.2 (C1), 30.3 (C2).

EXAMPLE 4

Preparation of Optically Pure 1-Deoxynojirimycin and 1-Deoxymannojirimycin (a) Preparation of Optically Pure Aldehyde To prepare optically pure D- and L-3-azido-2-hydroxypropanal, the reaction shown in the following scheme was performed:

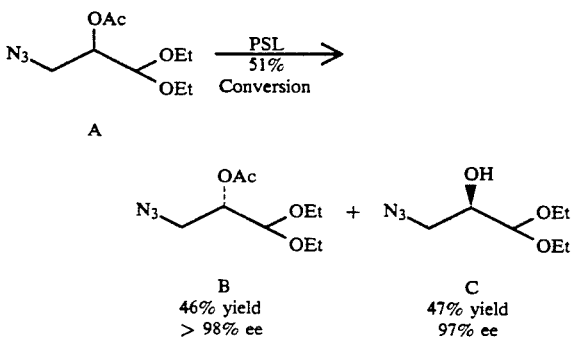

B
46% yield
> 98% ee

C
47% yield
97% ee 3-azido-2-hydroxypropanal diethylacetal acetate (10 mmol) was suspended in 100 mL of a sodium phosphate buffer (0.05M, pH 7) and stirred with 100 mg of Pseudomonas lipoprotein lipase (PSL) (purchased from Amano International Enzyme Co., and obtained from other chemical companies) for 10 h. The mixture was extracted with ethyl acetate, evaporated, and chromatographed on a silica gel column (EtOAc:n-hexane=1:12 1:8) to give 1.06 g (46%) of unreacted substrate B and 0.89 g (47%) of hydrolyzed product C. The optical purity of B was determined to be greater than 98% by $^1$H-NMR analysis in the presence of Eu(hfc)₃. The relative intensities of the acetoxy group at 3.52 (major) and 3.57 (minor) were used for % ee determination. To determine the ee of C, C was converted to (+)-2-methoxy-2-(trifluoromethyl) phenylacetate ester ((+)-MTPA ester) and analyzed by $^1$H-NMR according to the procedures set out in Dale, J. A., Dull, D. L., Mosher, H. S. *J. Org. Chem.* 34 (1969) 2543, to establish an ee of 97%. The relative intensities of the methine proton of the acetal group at 4.66 (d major) and 4.54 (d minor) were measured for the determination. To prepare optically pure D- and L-3-azido-2-hydroxypropanal, B first was treated with 1N NaOH to remove the acetate ester followed by acid hydrolysis (0.1N, HCl) to remove the acetal group, and C was treated with acid. Based on the aldol product obtained, B has an S- [or L-] and C has an R- [or D-] configuration.

(b) Synthesis of 1-deoxymannojirimycin

The general scheme of the following reactions is:

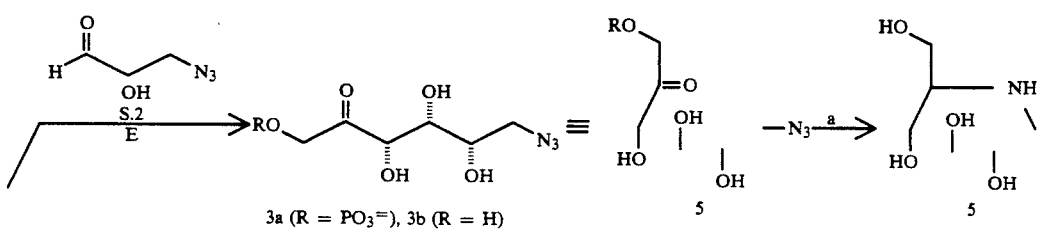

3a (R = PO₃⁼), 3b (R = H)

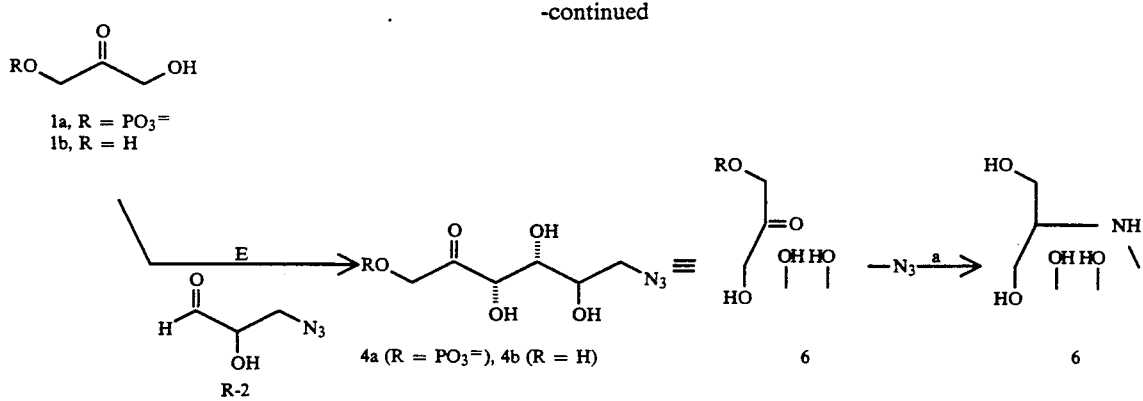

(i) A solution of (50 mL) containing (R)-3-azido-2-D-hydroxypropanal (12 mmol), triosephosphate isomerase (500 U) (purchased from Sigma), FDP-Na₃ (purchased from Sigma) (3.0 mmol), $Zn^{+2}$-FDP aldolase isolated from E. coli (16 U) at pH 6.5 was stirred slowly for 48 h. The product was recovered as its barium salt and the phosphate moiety was removed by treatment with phosphatase as already described. The sugar obtained was then hydrogenated in 50% MeOH with 300 mg 10% Pd/C under 40 psi of hydrogen for 10 h. The solution was filtered, concentrated to 4 mL chromatographed on a Dowex 50 $Ba^{+2}$ column (3.0×97 cm) with water as the mobile phase, and the product was eluted (356–430 mL). Lyophilization yielded 0.80 g, 80% yield; $[\alpha]_D^{25} = -29$ (c 0.2, MeOH). The $^1$H-NMR spectra, optical rotation, and microanalysis was in agreement with reported values for deoxymannojirimycin.

(ii) Synthesis of 1-Deoxynojirimycin

The procedure outline in Example 4 (b)(1) was repeated using (S)-3-azido-2-L-hydroxypropanal as the aldehyde acceptor. Lyophilization yielded deoxynojirimycin (0.48 g, 50 % yield, $[\alpha]_D^{25} = +47.5$ (c 0.2 H₂O)) The $^1$H-NMR spectra, optical rotation, and microanalysis was in agreement with reported values.

Examples 4 (b)(i) and (b)(ii) were repeated using rabbit muscle FDP aldolase (purchased from Sigma), and similar results were obtained.

EXAMPLE 5

Preparation of 1-Deoxynojirimycin and 1-Deoxymannojirimycin Using Dihydroxyacetone and Sodium Arsenate To a solution of D,L-3-azido-2-hydroxypropanal (6, mmol, prepared as in Example 1(a)) in 12 ml of water, was added 12 ml of a 1.0M sodium arsenate (Na₃AsO₄) pH 7.5, 270 mg (1.5 mmol) dihydroxyacetone (DHA), and 72 μl of a 0.1M zinc chloride (ZnCl₂). The pH was adjusted to 6.5 with 2N NaOH. FDP aldolase from E. coli (16 U) was added and the solution was stirred slowly for 14 hrs. The product solution was diluted with 100 ml of methanol and centrifuged (the sodium arsenate precipitates out of solution). The methanol was removed under reduced pressure, and the solution was concentrated to 5 ml and chromatographed on a Dowex 50 ($Ba^{+2}$) 100–200 mesh column (3×97 cm) using a mixture of ethanol and water (1:1) as the mobile phase. The fractions with the precursor product were combined and the ethanol was removed under reduced pressure. To the remaining solution was added ½ of its volume of methanol and the solution was hydrogenated with 300 mg of 10% Pd/C under 40 psi of hydrogen for 12 hrs. The catalyst was removed by filtration and the methanol was removed under reduced pressure. The remaining solution was concentrated to 5 ml and chromatographed on a Dowex 1 (OH⁻) column. The fractions with product were collected and lyophilized to yield 298 mg, 61% yield (based on DHA) of a white compound. $^{13}$C-NMR indicated a 1:2.3 ratio of 1-deoxynojirimycin and 1-deoxymannojirimycin. All physical properties are consistent with those reported.

Rabbit muscle FDP aldolase can be used in place of FDP from E. coli to obtain similar results. If rabbit muscle FDP is used, no ZnCl₂ is required. If optically pure aldehyde is used, optically pure alkaloid is obtained.

EXAMPLE 6

Preparation of 6-Deoxy-6-Trifluoroacetamido-D-Arabino-Hexulose

The N-containing aldehyde acceptor can contain nitrogen in forms other than as an azido- moiety. The following is an example describing formation of a protected sugar from an aldehyde acceptor having a protected amino group.

(D,L)-3-Amino-2-Hydroxypropanal Diethyl Acetal

To a suspension of Pd/C (10%, 0.5 g, 0.5 mmol) in 150 ml ethanol was dissolved (D,L)-3-azido-2-hydroxypropanal diethyl acetal (8.04 g, 39 mmol). The mixture was degassed and hydrogenated under a hydrogen balloon for 24 hr. The reaction was monitored by GC (50°-1 min to 250°-5 min at 15° C./min, DB-5; retention time of azide=7.4 min, amine=6.4 min). The ethanol was removed under reduced pressure and the residue distilled to yield (D,L)-3-amino-2-hydroxypropanal diethyl acetal (5.3 g, 33 mmol, 83%, bp₀.₀₃=59°. Solidified upon cooling, mp=45°). $^1$H-NMR (200 MHz, DMSO) δ 1.08, 1.10 (t, J=7.0 Hz, 6H, CH₃), 2.41 (dd, J=7.4 Hz, J=13.0 Hz, 1H, CH—N), 2.62 (dd, J=3.8 Hz, J=13.0 Hz, 1H, CH—N), 3.27 (ddd, J=3.8 Hz, J=7.4 Hz, J=6.0 Hz, 1H, CH—O), 3.35–3.69 (m, 4H, CH₂O), 4.21 (d, J=6.0 Hz, 1H, CH). $^{13}$C-NMR (50 MHz, DMSO) δ 15.32, 15.39 (CH₃), 43.63 (CH₂NH₂), 61.72, 62.48 (CH₂O), 72.51 (CHO), 103.83 (CH).

(D,L)-2-Hydroxy-3-Trifluoroacetamidopropanal Diethyl Acetal

To 30 mL of ethyl trifluoroacetate (250 mmol) was added (D,L)-3-amino-2-hydroxypropanal diethyl acetal (4.25 g, 26 mmol). The reaction was over immediately as determined by GC (same as described above, retention time of amide=8.1 min). The solvent was removed under reduced pressure and the residue distilled to yield (D,L)-2-hydroxy-3-trifluoroacetamidopropanal diethyl acetal (5.1 g, 19.7 mmol, 76% bp$_{0.05}$=62°. The sample solidified upon cooling, mp=42°). $^1$H-NMR (200 MHz, DMSO) δ 1.10, 1.11 (t, J=7.0, 6H, CH$_3$), 3.14 (ddd, J=13.3 Hz, J=8.6 Hz, J=6.0 Hz, 1H, CH—N), 3.33 (ddd, J=13.3 Hz, J=3.5 Hz, J=6.0 Hz, 1H, CH—N), 3.40–3.72 (m, 5H, CH$_2$O, CHO), 4.25 (d, J=4.5 Hz, 1H, CH), 5.05 (d, J - 5.6 Hz, 1H, OH), 9,22 (t, J=6.0 Hz, 1H, NH). $^{13}$C-NMR (50 MHz, DMSO) δ 15.22, 15.31 (CH$_3$), 41.59 (CH$_2$N), 62.12, 63.02 (CH$_2$O), 68.87 (CHO), 103.67 (CH), 116.03 (q, J=288 Hz, CF$_3$), 156.4 (q, J=36 Hz, C=O). Anal. Calc. C(41.7), H(6.2), N(5.4), found C(41.9), H(6.2), N(5.6).

6-Deoxy-6-Trifluoroacetamido-D-Arabino-Hexulose

Into a solution of 15 mL H$_2$O and 200 μl of HCl was dissolved (D,L)-2-hydroxy-3-trifluoroacetamidopropanal diethyl acetal (1.036 g, 4 mmol). The solution was warmed to 38° C. for 15 hrs. The reaction was monitored by GC (as described earlier). After complete hydrolysis of the acetal, FDP (593 mg, 1.08 mmol) was added and the pH adjusted to 6.8 with NaOH. The solution was degassed with argon and aldolase (300 U) and TPI (500 U) were added. Twenty hours later, the reaction was complete. The sugar was isolated as described earlier to yield the titled compound.

The foregoing description has been for purposes of illustration only. Those skilled in the art will appreciate a number of variations and modifications therefrom. The following claims are intended to cover all modifications and variations within the true spirit and scope of the present invention.

What is claimed is:

1. A compound having the following stereospecific structure:

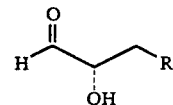

wherein R is N$_3$.

2. A compound having the following stereospecific structure:

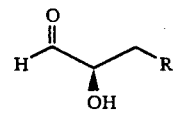

wherein R is N$_3$.

* * * * *

UNITED STATES PATENT AND TRADEMARK OFFICE
CERTIFICATE OF CORRECTION

PATENT NO. : 5,329,025
DATED : July 12, 1994
INVENTOR(S) : Wong, et al.

It is certified that error appears in the above-indentified patent and that said Letters Patent is hereby corrected as shown below:

Column 3, line 37, reading "Sweets, H.M.," should read -- Sweers, H.M., --.

Column 6, line 1, the formula reading

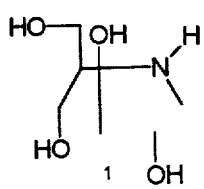 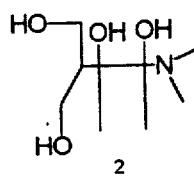 should read 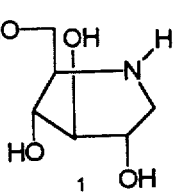 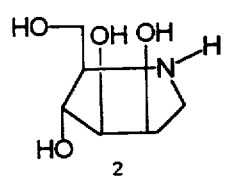

Column 7, line 15, reading "Sweets, H.M.," should read -- Sweers, H.M., --.

Column 7, line 54, reading "1,4-amino-" should read -- 1,4-imino- --.

Column 9, line 37, the formula reading

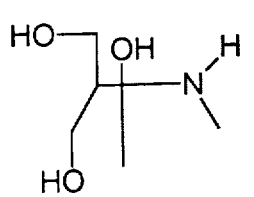 should read 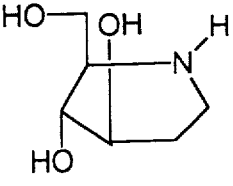

UNITED STATES PATENT AND TRADEMARK OFFICE
CERTIFICATE OF CORRECTION

PATENT NO. : 5,329,025       Page 2 of 2
DATED : July 12, 1994
INVENTOR(S) : Wong, et al.

It is certified that error appears in the above-indentified patent and that said Letters Patent is hereby corrected as shown below:

Column 10, line 60, the formula reading

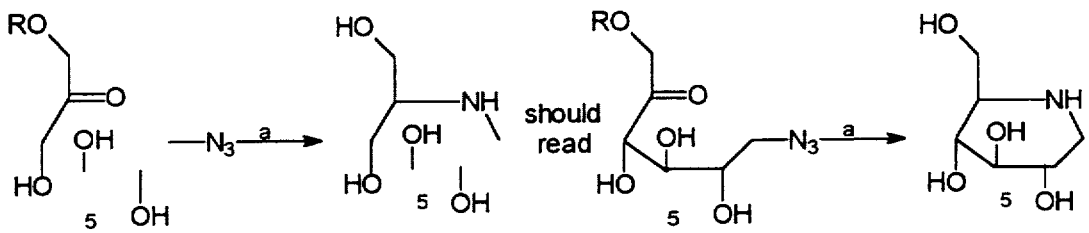

Column 12, line 10, the formula reading

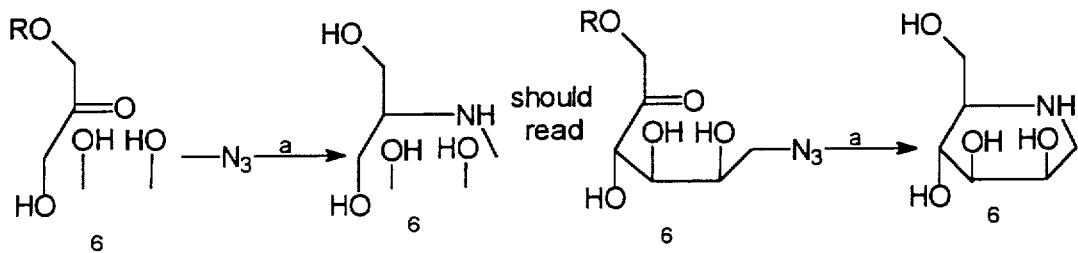

Signed and Sealed this

Seventeenth Day of October, 1995

Attest:

BRUCE LEHMAN

Attesting Officer     Commissioner of Patents and Trademarks